United States Patent [19]

Redziniak et al.

[11] Patent Number: 4,508,703

[45] Date of Patent: Apr. 2, 1985

[54] PRODUCTION OF PULVERULENT MIXTURES OF LIPIDIC AND HYDROPHOBIC CONSTITUENTS

[75] Inventors: Gérard Redziniak, Sartrouville; Alain Meybeck, Courbevoie, both of France

[73] Assignee: Parfums Christian Dior, France

[21] Appl. No.: 465,598

[22] Filed: Feb. 10, 1983

[30] Foreign Application Priority Data

Feb. 17, 1982 [FR] France .................................. 82 02620

[51] Int. Cl.³ ........................ B01J 13/00; A61K 9/42
[52] U.S. Cl. .................................. 424/38; 428/402.2; 264/4.6; 436/829; 424/64; 424/69; 424/94; 424/95; 514/195.1; 514/78; 514/458; 514/776; 514/773; 514/784; 514/785
[58] Field of Search ...................... 428/402.2; 436/829; 264/4.6; 424/38

[56] References Cited

U.S. PATENT DOCUMENTS 3,207,666  9/1965  Houtgraaf et al. .................. 436/829
3,499,962  3/1970  Wurzburg et al. ............... 428/402.2
4,235,792 11/1980  Hsia et al. ........................... 436/829

FOREIGN PATENT DOCUMENTS 1575334  9/1980  United Kingdom .
2066203  7/1981  United Kingdom ................ 436/829

*Primary Examiner*—Ben R. Padgett
*Assistant Examiner*—Anne Brooks
*Attorney, Agent, or Firm*—Steinberg & Raskin

[57] ABSTRACT

The invention relates to a method for preparing a pulverulent mixture of amphiphilic lipidic constituents and possibly of hydrophobic constituents, as well as to a method for producing hydrated lipidic lamellar phases from the pulverulent mixture.

The method comprises dissolving the amphiphilic lipidic constituents and the hydrophobic constituents in an appropriate solvent and then atomizing said solution in a flow of gaseous fluid to produce the pulverulent mixture. The mixture thus obtained is a homogeneous and very fine powder which can be very easily dispersed in a suitable aqueous dispersion medium to produce either slightly hydrated lipidic lamellar phases or highly hydrated lipidic lamellar phases such as liposomes useful in the pharmaceutical and cosmetic fields.

34 Claims, No Drawings

PRODUCTION OF PULVERULENT MIXTURES OF LIPIDIC AND HYDROPHOBIC CONSTITUENTS

BACKGROUND OF THE INVENTION

The present invention relates generally to hydrated lipidic lamellar phases and to a method for obtaining the same, and also to compositions intended particularly for pharmaceutical, cosmetic or like uses and comprising said lipidic lamellar phases.

The present invention is more specifically directed to a method for obtaining pulverulent mixtures of amphiphilic lipidic constituents and hydrophobic constituents, the said mixture being used particularly for producing hydrated lipidic lamellar phases.

The hydrated lipidic lamellar phases have been described amply in scientific publications, notably by R. PERRON ("Revue Francaise du Corps Gras", 1980, 27 (4) 173-183). Their formation results from a property which is typical of certain amphiphilic lipids in the presence of an aqueous medium. The amphiphilic lipid molecules are composed of a polar or non-polar hydrophilic portion and of a hydrophobic portion. According to M. M. RIEGER ("Cosmetics and Toiletries", 1981, 96 35-38), one of the conditions for the amphiphilic lipid to be capable of forming lamellar phases rather than only micellar clusters is that the dimensions of its hydrophobic portion be at least as important as that of its hydrophilic portion.

Such lipids are capable of forming bimolecular lipidic layers (lamellae or bilayers), separated from one another by a more or less important amount of water or of aqueous solution which may be reduced to a mere interstitial film. The molecules of said lipids forming the lipidic layers are placed side by side and so oriented that their hydrophobic portion is located inside the layer. The lipidic layers and interstitial aqueous medium as a whole are referred to as a hydrated lipidic lamellar phase.

The liposome is a particular configuration of a lamellar phase appearing in the form of a lipidic spherule composed of one or several concentric bilayers alternating with aqueous compartments. The liposomes are dispersed in an aqueous medium and form a highly hydrated lamellar phase. The conditions under which non-polar amphiphilic lipids can form liposomes or "niosomes" have been set forth by G. VANLERBERGHE et al. ("Colloques Nationaux du CNRS", N° 938, Bordeaux 1978, CNRS Publications, 1979, pages 303-311).

It is also known that liposomes can be obtained by dispersing in an aqueous medium a lamellar phase by various methods, notably by means of ultrasonic waves.

Liposomes have been dealt with in a great number of publications, such as for example in the articles already mentioned and in the following articles: Sessa G. et al., "J. Lipid Res." 1968, 9, 310-318; Bangham A. D. et al., "Meth. Membr. Biol." 1974, 1-68; D. A. Tyrrell et al., "Biochim. Biophys. Acta" 1976, 457, 259-302; Strianse S. J., "Cosmetics & Toiletries" 1978, 93, 37-41; Puisieux F., "Labo-Pharma" 1978, 281, 899-904; Nicolau C. et al., "La Recherche" 1981, 123, 748-749.

The commercial interest of liposomes or of hydrated lamellar phases lies in the fact that substances possessing interesting properties may be incorporated either in the lipidic bilayers in the case of the partially or totally hydrophobic substances, or in solution, in the aqueous medium located between two bilayers, or encapsulated in liposomes in the case of the water-soluble substances.

These products find numerous applications, particularly in the production of foodstuffs, cosmetic or pharmaceutical products.

Widely different substances may be incorporated in the lamellar phases or the liposomes, notably for the purpose of protecting damageable substances from external agents or of improving the penetration of certain substances into the biological tissues. It is also possible to modify the physico-chemical properties of the lamellar phases or the liposomes themselves by incorporating into the lipidic bilayers certain compounds such as sterols, e.g. cholesterol (G. Vanderberghe et al., supra; G. Gregoriadis, "Biochem J", 19, 196, 591) for the purpose, in particular, of controlling the permeability and stability of the lipidic bilayers.

The addition of hydrophobic compounds such as sterols increases the hydrophobic group to hydrophilic group ratio, which complies with the condition of stability of the lamellar phases set forth by M. M. Rieger (supra). Thus, the addition of such hydrophobic compounds makes possible the formation of lamellar phases with amphiphilic lipids which could not form such phases used alone. It is also possible to incorporate into the lamellar phase amphiphilic compounds whose hydrophilic portion is charged positively or negatively (French patent applications No. 78-22985 and No. 78-13632); for example, dicetylphosphate imparts to the liposomes a negative charge, whereas stearylamine provides a positive charge.

A certain number of methods of production of such lamellar phases and of liposomes are already known. One of the methods most currently in use consists, in a first stage, in dissolving the amphiphilic lipid or lipids and possibly the hydrophobic substances or substances in an appropriate volatile solvent. The solution obtained is placed in the flask of a rotary evaporator. After the solvent is evaporated, a film adhering to the flask wall is obtained. Water or, if suitable, the aqueous solution to be encapsulated is introduced into the flask and the entire content is vigorously agitated. There is thus obtained a suspension of liposomes which, if appropriate, may be subjected to ultrasonic homogenization. One of the drawbacks to this method resides in that the film can be obtained only with great difficulty on a commercial scale.

According to another method described notably in French patent application No. 78-22985, the aqueous solution to be encapsulated is dispersed in a solvent which is insoluble or only slightly soluble in water in the presence of a lipid or of an amphiphilic surfactant. This results in the formation of microdrops of the said aqueous solution, which are thereafter emulsified in an aqueous medium in the presence of an excess of a lipid or surfactant which may be identical with or different from the one used previously. The insoluble solvent is eliminated before or after the emulsification, for example by blowing air at the surface of the liquid. This method requires a complete elimination of the solvent used, which involves numerous difficulties, especially on a commercial scale. Moreover, it does not allow for production of only slightly hydrated lamellar phases.

It is also possible to prepare liposomes according to the method of Swiss Pat. No. 623,236 by bringing into contact, on the one hand, at least one liquid amphiliphic lipid dispersible in water, the hydrophilous portion of which is ionic, and on the other hand, the aqueous phase to be encapsulated. The mixture is thereafter subjected to vigorous agitation to obtain a lamellar phase which thereafter may be dispersed in water or an aqueous solution. In this method, to incorporate hydrophobic compounds, it is necessary to use surface-active compounds whose emulsifying property is higher the more marked the hydrophobic character of the compound to be incorporated. Such surface-active compounds are very often incompatible with many applications of the liposomes, e.g. in the field of pharmacy or cosmetics.

According to another method described in French patent application No. 78-13632, a solution is prepared containing at least one amphiphilic lipid, at least one biologically active compound and, if suitable, at least one catalyst. This solution is lyophilized to eliminate the solvent and the mixture of the constituents is obtained in the form of powder which may be stored in sealed containers until it is used to form, in particular, liposomes. This last stage consists in dispersing the powder in an appropriate aqueous medium. This method suffers from the drawbacks involved particularly in the conventional lyophilizing techniques which are relatively complex and expensive and the production rate of which is moreover relatively limited.

The various known methods described above therefore suffer from many drawbacks which, do not allow, in particular, easy or inexpensive production of lamellar phases on a commercial scale. These drawbacks are mainly due to the difficulties of obtaining a thorough mixture of the basic constituents forming the lamellar phases, in other words the amphiphilic lipids and possibly the hydrophobic substances. In order to facilitate the dispersion of the basic constituents of the lamellar phases in an aqueous medium, it is often necessary to use additional products with surface-active properties. Since such products often have undesirable effects, e.g. with respect to the organism, it is necessary to eliminate them completely, which is not always possible even by way of dialysis. "Basic constituents" means the compounds used to form the lipidic layers of the lipidic lamellar phase, namely, at least one amphiphilic lipid or a mixture of one or several amphiphilic lipids and, possibly, one or several partially or totally hydrophobic compounds.

SUMMARY OF THE INVENTION

The purpose of the present invention is to remedy the above drawbacks by providing a new method for obtaining hydrated lipidic lamellar phases, and more particularly a new method for obtaining a pulverulent mixture of amphiphilic lipidic constituents with, possibly, hydrophobic or partially hydrophobic constituents. This method is of great simplicity and allows continuous production of large quantities of mixtures and therefore of hydrated lipidic lamellar phases or of liposomes, without however requiring, in particular, the use of additional products with surface-active properties.

To this end, the present invention is directed to a method for obtaining a pulverulent mixture of at least one amphiphilic lipidic constituent and possibly of at least one constituent of hydrophobic or partially hydrophobic character, said mixture being used in particular for the formation of hydrated lipidic lamellar phases such as for example liposomes, or the like, said method consisting in dissolving the amphiphilic lipidic constituent or constituents and, possibly, the hydrophobic constituent or constituents in a solvent to form a solution of the said constituents, characterized in that said solution is atomized in a flow of gaseous fluid to produce the said pulverulent mixture. Thus, it is possible to obtain an extremely fine powder which can be easily dispersed in an aqueous medium by the known methods of dispersion to form a lamellar phase which is more or less hydrated depending on the ratio of the quantity of dispersed product to the quantity of aqueous medium used.

Moreover, this method allows for obtaining a powder product which can be easily stored for future use, thus enabling the hydrated lipidic lamellar phase to be produced through dispersion of the powder in a suitable aqueous medium containing, if appropriate, an active compound to be encapsulated immediately before its use, for example as a medicine or as a treating product in dermatology, cosmetics or the like. The method of the present invention is particularly advantageous when the encapsulated compound with an interesting active property is relatively unstable and can be prepared only immediately prior to its use.

The method of the invention therefore comprising dissolving in a solvent or a mixture of appropriate solvents the basic constituents, in other words at least one amphiphilic lipid and possibly one hydrophobic or partially hydrophobic constituent desired to be incorporated into the lipidic bilayers.

The solution obtained is thereafter atomized. This operation particularly comprises introducing the solution, in the form of very fine droplets, e.g. by means of a spray nozzle or atomizer, into an enclosed space traversed by a gaseous fluid heated to a temperature higher than the boiling point of the solvent used. The solvent is vaporized under the action of heat and is entrained by the gaseous flow. In the region provided in the apparatus where the temperature of the gaseous fluid flow falls below the temperature of transition of the mixture of said basic constituents, an extremely fine powder is formed, this powder being recovered by a device such as for example a cyclone and collected at the bottom of this device. The collected mixture of basic constituents dissolved in the initial solution is homogeneous and constituted by extremely fine particles.

Thus, the method of the invention allows treating important quantities of solution and therefore producing on a commercial scale a pulverulent mixture which can be used in particular for the production of hydrated lipidic lamellar phases such as liposomes or the like. Indeed, since the basic constituents are dissolved in a solvent, no problem of agitating a large volume of solution arises and it is possible to atomize a relatively important flow of solution without using complex and expensive apparatus. Moreover, the energetic power necessary for atomizing a solution and evaporating the solvent is markedly smaller than the energetic power consumed by the prior lyophilizing technique.

Advantageously, the temperature of atomization is comprises between about 60° C. and about 100° C.

It is of course possible, according to the method of the invention, to atomize a solution containing only one costituent, i.e. an amphiphilic lipid, if it is desired to produce lipidic bilayers constituted by this single constituent. However, the more commonly used lipidic bilayers comprise a mixture of several constituents, e.g. at least one amphiphilic lipidic constituent and, possibly, at least one hydrophobic or partially hydrophobic constituent.

DETAILED DESCRIPTION OF THE PREFERRED EMBODIMENTS

Any amphiphilic lipid capable of forming lamellar phases can be used in the method of the invention. However, it is necessary that such amphiphilic lipids used either alone or in the presence of partially or totally hydrophobic substances be suitable for atomization, i.e., that the temperature of transition of the amphiphilic lipid or of the mixture be suitable for obtaining an atomized product in the form of powder.

In the case of production of a mixture containing at least one hydrophobic or partially hydrophobic substance, in order to allow the formation of lamellar lipidic phases, the weight proportion of the amphiphilic lipidic constituent or constituents in the total of the basic constituents dissolved in the initial solution (i.e., the total of the amphiphilic lipidic constituents and the hydrophobic constituents), must be at least greater than 50%, and preferably greater than about 70%.

As a suitable amphiphilic lipid, compounds selected from the group consisting of phospholipids, glycolipids or phosphoaminolipids such as for example an egg or soja lecithin, a phosphatidylserine, a cerebroside or a sphyngomyelin, can be used.

The hydrophobic or partially hydrophobic substances which are suitable for mixing with at least one amphiphilic lipidic substance in the solution prior to atomizing, are extremely varied and are selected according to the properties which are sought to be imparted, on the one hand, to the pulverulent mixture, and on the other hand, to the lamellar phases or the liposomes produced from the pulverulent mixture.

By way of example, as hydrophobic or partially hydrophobic substances, use can be made of sterols or esters thereof, such as cholestrol, $\beta$-sitosterol, oestradiol, lanosterol, stigmasterol, $\gamma$-oryzanol; aliphatic fatty acids or esters thereof such as for example steraric acid, ximeninic acid, isopropyl myristate or the like; triterpenic fatty acids or esters thereof such as for example glycyrrhetinic acid or the like; primary or secondary fatty acids or esters thereof such as for example dicetyl phosphate; aliphatic fatty amines such as for example stearylamine; aminated acids acylated with a fatty acid such as for example stearoly-L-glutamic acid; polypeptides such as for example elastin hydrolysate polypeptides; vitamins, for example a tocopherol, advantageously an $\alpha$-tocopherol; extracts of animal or vegetable origin such as for example embryonic extracts or aloe extracts; or phenols which may comprise one or several substituents selected from the radical groups including alboxy, alkyl comprising from 1 to 4 carbon atoms, carboxy, formyl, such as for example vanilline.

However, this list of hydrophobic constituents which can be used to form a pulverulent mixture according to the method of the invention is not limited.

Moreover, it may be advantageous, though not absolutely necessary, to select as an amphiphilic lipidic constituent and/or as hydrophobic constituent, a compound that is biologically active and/or possesses interesting organoleptic and/or physicochemical properties.

Furthermore, the solvent for preparing the solution to be atomized is selected, on the one hand, according to its dissolving capacity with respect to the above-described basic constituents, and on the other hand, depending on its boiling point which must be too high in order to avoid using an atomization temperature which would result in deteriorating the basic constituents. It is also possible, according to the invention, to use a mixture of solvents that are miscible with one another, in the proper proportions to meet the conditions set forth above. This dissolution of the constituents is performed before or after the mixing of the solvents, and may require a slight heating, e.g. at a temperature of about 40° C.

The solvents currently used are, particularly, chloroform, methanol, ethanol, dichloromethane, or a mixture of chloroform with methanol or of chloroform with ethanol, containing 33% methanol or ethanol, respectively.

According to another characterizing feature of the invention, the gaseous fluid used in the atomizing process must be substantially and chemically inert in regard to the basic constituents dissolved in the initial solution. However, since the atomizing step is of relatively short duration, with the time during which the basic constituents and the carrier gas are in mutual contact being very short, it is generally possible to use air without incurring the risk of oxidation of the said constituents. Of course, it may be necessary to select gases that are more inert than air, e.g. nitrogen or the like, especially in case the temperature of atomization is relatively high or where one of the basic constituents is very sensitive to oxidation.

Advantageously, the gas flow rate is so adjusted to prevent a portion of the powder formed from being lost in the flow of gaseous fluid.

As described previously, the gaseous fluid at the inlet into the atomizing apparatus, must be at a temperature referred to as the atomizing temperature, which is higher than the boiling point of the solvent used.

However, the temperature of this gaseous fluid must not prevent the formation of the powder in the region provided therefor in the apparatus, i.e., the gaseous fluid in the said region must be at a lower temperature than the temperature of transition of the mixture of constituents dissolved in the initial solution.

According to a variation of the method of the invention, prior to atomization, fine solid microalveolate particles, e.g. kieselguhr, are added to the lipidic solution in an amount at least equal in weight to that of all the lipids contained in the solution and preferably at least thrice as great as the amount of lipids.

Of course, a further amount of solvent will be added, if need be, so that the final suspension may be vaporizable in the atomizing apparatus.

Furthermore, the dimensions of the solid particles must not be too large in order to avoid obstructing the spraying nozzle or atomizer of the apparatus.

As a result of the atomization, the lipidic complex is intimately mixed with the solid particles in the form of powder.

One advantage of this variation of the method is that it allows a powder to be obtained through atomization even by using amphiphilic lipids whose melting temperature is lower than 50° C.

Of course, the methods for producing a pulverulent mixture according to the invention may be carried out either continuously or discontinuously, the powder being collected directly at the outlet of the cyclone, either to be stored as a product or to be used immediately, in particular for the formation of hydrated lamellar phases such as liposomes.

The invention is also directed to a pulverulent mixture of lipidic constituents with possibly at least one hydrophobic or partially hydrophobic constituent obtained by the above-described method. A particular property of this mixture is that it is very easily dispersible in an aqueous solution.

The invention is also directed to a method for producing hydrated lipidic lamellar phases such as liposomes or the like, characterized in that it comprises dispersing the above-described pulverulent mixture in an appropriate aqueous medium.

The pulverulent mixture obtained through atomization is dispersed in the aqueous medium by a conventional method such as for example stirring, homogenization or sonication.

However, the pulverulent mixture obtained according to the variation of the atomizing process of the invention, dispersed by means of mere agitation, e.g. by means of a magnetic bar, allows a highly hydrated phospholipidic lamellar phase to be obtained comprises particles in the form of liposomes of greatly reduced dimensions, on the order of from 100 to 300 nanometers, without it being necessary to use the usual homogenization techniques, such as for example ultrasonication.

The solid microalveolate particles contained in the said dispersion may be readily eliminated through mere filtration, for example on a 10 μm porous filter, which filtration may be followed, if necessary, by a sterilizing filtration.

Advantageously, the aforesaid pulverulent mixture may be collected directly in the container where the dispersion in the aforesaid aqueous medium takes place, downstream of the means of recovery of the powder, e.g. downstream of the cyclone, in its lower portion. Thus, a continuous production of either slightly hydrated lamellar phases or of liposomes is performed.

The various aqueous media used for preparing hydrated lamellar phases may be either water, or solutions of various substances, the choice of which depends upon the properties desired to be imparted to the hydrated lamellar phases. For example, the aqueous solution intended to be encapsulated in the lamellar phases or liposomes may contain substances having interesting biological, organoleptic, physicochemical or physiological properties. By way of non-limitative example, the solution to be encapsulated may contain enzymes, antibiotics, polypeptides such as elastin polypeptides. The dispersion medium may also be an isotinic solution of sodium chloride.

According to a first form of an embodiment of the invention, it is possible to disperse a pulverulent mixture obtained through atomization directly in a relatively important amount of aqueous medium to obtain directly the desired weight concentration of lamellar phases.

For example, the atomized pulverulent mixture is dispersed in an aqueous medium in which, if desired, a substance to be encapsulated is dissolved to obtain a weight concentration of the pulverulent mixture in the suspension lower than about 50%. A suspension is thus obtained of highly hydrated lamaller phases in which the dissolved substance is encapsulated. Suspensions with a weight concentration of pulverulent mixture between about 10% and about 25% are preferred.

Thus, the efficiency of encapsulation of the substance dissolved in the aqueous medium is between about 20% and about 50%. This encapsulation efficiency is high, for it is possible, in order to obtain hydrated lamellar phases, to disperse the atomized pulverulent mixture in a relatively small quantity of aqueous medium.

According to a variation of the method of the invention, the atomized pulverulent mixture is dispersed in a relatively small amount of an aqueous medium advantageously containing the substances desired to be encapsulated, the dispersion being homogenized to ensure a very good mixing, for example by means of a roller mill. The weight concentration of the pulverulent mixture in the mixture obtained is for example higher than approximately 50%. There is thus obtained a slightly hydrated lamellar phase.

This lamellar phase may be used directly as commercial products, in which case the weight concentration of pulverulent mixture is advantageously between about 60% and about 70%. Alternatively, this slightly hydrated lamellar phase may be diluted in a fresh amount of the aqueous medium already used, or in a fresh aqueous dispersion medium, to form a highly hydrated lamellar phase, i.e. a suspension of liposomes, to advantageously obtain a weight concentration of pulverulent mixture between about 0.1% and about 10%. Thus, in this variation, a very high encapsulation efficiency, exceeding about 50%, is obtained.

According to a preferred form of an embodiment of the invention, the aforesaid aqueous dispersion medium is isoosmotic in regard to the aqueous solution to be encapsulated.

Furthermore, this method allows for obtaining lamellar phases or liposomes of very small size, e.g. smaller than or equal to three microns, a size confirmed by electron-microscope examination.

It is also possible, if desired, to obtain a more thorough homogenization of the liposome suspension, e.g. by means of prolonged sonication.

The present invention is also directed to hydrated lipidic lamellar phases such as liposomes or the like obtained according to the above-described method. Advantageously, the lamellar phases contain encapsulated substances possessing useful properties, notably in the pharmaceutical, cosmetic, foodstuff production and other fields.

Lastly, the invention is also directed to pharmaceutical or cosmetic compositions containing lipidic lamellar phases produced according to the above method, notably as a vehicle for active substances.

According to the methods of the invention, it is possible to obtain an intimate mixture of the basic constituents of the lipidic lamellar phases, namely, a mixture of one or several amphiphilic lipidic compounds and of one or several hydrophobic compounds, without it being necessary to use additional compounds such as surface-active compounds. Furthermore, it is possible to produce hydrated lipidic lamellar phases from the atomized pulverulent mixture of the invention, by dispersing the latter in a relatively small amount of aqueous medium and, therefore, obtaining a high efficiency of encapsulation of the compounds dissolved in the aqueous medium.

Also, these methods allow for producing hydrated lipidic lamellar phases according to a continuous or discontinuous method of production. Moreover, they may be used very easily on a commercial scale at a smaller production cost than that of the known methods.

Furthermore, the pulverulent mixture obtained as a result of atomization may be easily dispersed in an aqueous medium, thus allowing slightly hydrated lipidic lamellar phases or highly hydrated lipidic lamellar phases to be obtained.

The invention will be better understood and other characterizing features, details and advantages thereof will appear more clearly from the following non-limitative examples given solely by way of illustration of the present invention.

EXAMPLE 1

9 g of phosphatidylserine and 1 g of beta-sitosterol are introduced into a 100 ml beaker and are dissolved therein by means of magnetic stirring in 50 ml of chloroform. To the solution obtained (solution A) is added, under continued stirring, 0.1 g of sodium stearoylglutamate in solution in 25 ml of methanol (solution B). The mixture obtained is vaporized within an atomizing device supplied with air at a temperature adjusted to 75° C. A very fine white powder is collected in a receptacle placed at the base of the apparatus.

The powder thus obtained is introduced into a 500 ml beaker containing 100 ml of a solution comprising '% hyaluronidase and 0.9% sodium chloride (solution C). The homogenization of the mixture is performed at standard temperature by means of magnetic stirring for one hour. There is obtained a dispersion having a gel-like appearance. The latter is poured into a 1.5 l container provided with propeller mixing and is diluted in 900 ml of a physiological solution (0.9% aqueous solution of sodium chloride). An opalescent suspension is thus obtained.

Electron-microscope examination of this suspension reveals the the presence of liposomes smaller than 3 microns in size.

EXAMPLE 2

9.9 g of sphingomyelin and 0.1 g of dicetyl phosphate are introduced into a 100 ml beaker containing a mixture of 50 ml chloroform and 25 ml of methanol and are stirred therewith. The solution obtained is atomized as in the foregoing example at 75° C. The powder collected at the outlet of the apparatus is intimately mixed with 100 ml of an aqueous solution of 1% alpha-chymotrypsin and 0.9 % sodium chloride, by means of magnetic stirring for one hour followed by sonication for 20 minutes. As in the foregoing example, a dilution is performed in 900 ml of a physiological solution. There is obtained a blueish solution. The size of the liposomes, determined by evaluating the Brownian movement of the particles (apparatus of the Nano-Sizer type), is slightly smaller than 0.1 micron. The efficiency of encapsulation of the alpha-chymotrypsin is determined after filtrating the blueish solution on gel (sepharose (CL-4B). The efficiency of encapsulation of the alpha-chymotrypsin with respect to the alpha-chymotrypsin dissolved in the aqueous dispersin solution is 40%.

EXAMPLES 3 TO 9

Liposomes are produced according to the method described in Example 1, with the constituents indicated in the appended Table 1.

TABLE 1

| Ex. N° | SOLUTION A in 50 ml of chloroform | | | | SOLUTION B in 25 ml of methanol | | C° Atomization °C. | SOLUTION C Quantity used 100 ml nature of products and concentrations |
|---|---|---|---|---|---|---|---|---|
| | Nature of product | weight (g.) | nature of product | weight (g.) | nature of product | weight (g.) | | |
| 3 | Cerebroside | 8 | Cholesterol | 2 | None | — | 75 | 0.1% Streptomycin 0.9% Na Cl |
| 4 | Soya lecithin | 9 | β-oestradiol | 1 | None | — | 75 | 0.9% Na Cl |
| 5 | Soya lecithin | 9.9 | None | — | Vanillin | 0.1 | 60 | 0.9% Na Cl |
| 6 | Soya lecithin | 9 | δ-oryzanol | 1 | None | — | 80 | 0.9% Na Cl |
| 7 | Soya lecithin | 8 | Cholesterol | 2 | None | — | 75 | 10% aloe extract 0.9% Na Cl |
| 8 | Soya lecithin | 9.5 | Cholesterol | 0.5 | None | — | 75 | 1% elastin hydrolysate 0.9% Na Cl |
| 9 | Soya lecithin | 8.9 | Cholesterol α-tocopherol | 1 0.1 | None | — | 75 | 0.9% Na Cl |

EXAMPLE 10

2 g of soya lecithin and 0.2 g of sitosterol are introduced into a 100 ml beaker containing 30 ml of dichloromethane and are stirred therewith by means of a magnetic bar until complete dissolution is obtained. 7 g of kieselguhr are thereafter added and the stirring is continued for 5 minutes in order to obtain a homogeneous suspension.

This suspension is vaporized within an atomizer supplied with air at a temperature adjusted to 60° C.

A very light powder is collected.

The powder thus obtained is introduced into a 500 ml beaker containing an aqueous solution of 1% milk glycoproteins and 0.9% sodium chloride. The mixture is subjected to magnetic stirring and is thereafter filtered on a 10 μm porous filter. An opalescent liquid is thus obtained in which electron-microscope examination reveals the existence of a suspension of liposomes whose size, measured by means of an apparatus of the Nano-Sizer type, is on the order of 220 nanometers.

This suspension of liposomes may be sterilized through sterilizing filtration on a 0.45 μm filter.

EXAMPLE 11

An atomized powder is produced according to the method described in Example 1 from 15 g of soya lecithin and 3 g of lanosterol in 50 ml of chloroform. Atomization is conducted at 75° C. The pale yellow powder obtained is mixed, using a spatula, with 6 ml of an aqueous solution containing 5% sodium carboxylate pyrrolidone, 5% sodium lactate and 0.9% sodium chloride, after which the mixture is homogenized by means of a roller mill.

A lamellar phase is obtained having the consistency of a viscous gel whose characteristics are checked through X-ray diffraction. This lamellar phase can be used in this form, notably for preparing cosmetic products.

It is also possible to disperse this slightly hydrated lipidic lamellar phase in 200 ml of an aqueous solution containing 0.9% sodium chloride to obtain a suspension of highly hydrated lamellar phases or liposomes. The measured efficiency of encapsulation of the sodium carboxylate pyrrolidone is 60%.

EXAMPLE 12

0.17 g of elastin hydrolysate dissolved in 100 ml of 96% ethanol is introduced into a 500 ml beaker. Chloroform in an amount of 200 ml and 0.34 g of soya lecithin are thereafter added while stirring. The mixture is atomized at 80° C. The white powder obtained is placed in suspension in 50 ml of a physiological solution by means of magnetic stirring for one hour. Electron-microscope examination reveals the existence of liposomes smaller in size then one micron. Sonication of this suspension allows obtaining a blueish opalescent solution containing liposomes whose size does not exceed 0.2 micron.

EXAMPLE 13

90 g of soya lecithin and 10 g cholesterol are introduced into a 500 ml beaker. This mixture is dispersed in 400 ml of chloroform. The solution thus obtained is atomized at 75° C. The atomizate, which appears as a white powder, is directly collected in 1 liter of a 0.9% solution of sodium chloride, containing 1 g of superoxydismustase (S. O. D.), subjected to vigorous magnetic stirring. At the end of the atomization, the stirring is continued for 1 hour at room temperature. The milky suspension obtained is thereafter dispersed in 9 liters of of a 0.9% solution of sodium chloride. The dispersion obtained is agitated by means of a rotor and paddle homogenizer for 15 minutes at room temperature. Electron microscope examination reveals liposomes of medium size on the order of 1 micron.

EXAMPLE 14

5 g of soya lecithin, 4 g of cholesterol and 1 g of γ-oryzanol are introduced into a 100 ml beaker. The mixture is dissolved in 75 ml of chloroform. The solution thus obtained is atomized at 75° C. The atomizate is collected directly in 100 ml of a 0.9% solution of sodium chloride containing 1 g of a collagen hydrolysate. The mixture thus obtained is subjected to homogenization, whereafter the suspension obtained is dispersed in 900 ml of a 0.9% solution of sodium chloride.

EXAMPLE 15

4 g of soya lecithin, 4 g of sphyngomyelin and 2 g of cholesterol dissolved in 75 ml of chloroform are introduced into a 100 ml beaker. The solution thus obtained is atomized at 75° C. The atomizate is collected directly in 1 liter of a 0.5% solution of d-glucose. This solution is subjected to vigorous agitation for the purpose of homogenizing.

EXAMPLE 16

180 g of soya lecithin and 20 g of stigmasterol dissolved by means of magnetic stirring in 1 liter of dichloromethane ($CH_2Cl_2$), are introduced into a 2 l beaker.

The mixture obtained is vaporized within an atomizer supplied with air at a temperature adjusted to 60° C. A very fine, white powder is collected in a receptacle placed at the base of the apparatus. The powder obtained is introduced into a 50 l container containing 20 liters of a solution of 0.9% sodium chloride and 1% elastin polypeptides. The homogenization of the mixture is performed at room temperature by means of a turbine rotor for 1 hour.

The size of the particles measured with a nanosizer is on the order of 450 nm.

Electron-microscope examination of these particles shows the existence of liposomes.

The following Examples 17 to 22 illustrated compositions for use notably in cosmetics, obtained from suspensions of lamellar phases or from the lamellar phases themselves obtained by the method of the invention, which are mixed with an excipient compatible with the human body, especially with the skin, the formed suspension adapted to be applied to the skin. Thus, the active constituent is incorporated or encapsulated in the lamellar phases produced according to the method of the invention. The suspension or lamellar phase is mixed with a suitable excipient to produce for example creams, milks or balms capable of being applied, particularly to the skin.

According to a similar method, pharmaceutical compositions can also be produced, with the encapsulated or incorporated constituent having interesting properties from a biological or physiological point of view. Such compositions may be in solid, pasty or liquid form depending on the excipient or vehicle used.

EXAMPLE 17

| Preparation of moisturizing cream for skin care | | |
| --- | --- | --- |
| Composition: | Elastin suspension (according to Example 12) | 10 g |
| | Emulsified excipient oil in water | 90 g |
| Use: | Daily applications to the skin | |

EXAMPLE 18

| Cream with stimulating properties for skin care | | |
| --- | --- | --- |
| Composition: | Oryzanol suspension (according to Example 6) | 10 g |
| | Emulsified excipient oil in water | 90 g |
| Use: | Daily applications to the skin | |

EXAMPLE 19

| Cream with protecting properties for skin care | | |
| --- | --- | --- |
| Composition: | Tocopherol suspension (according to Example 9) | 10 g |
| | Emulsified excipient oil in water | 90 g |
| Use: | Evening applications for preparing the skin to exposure to weather conditions the next day | |

EXAMPLE 20

| Moisturizing milk for the body | | |
| --- | --- | --- |
| Composition: | Aloe-extract suspension (according to Example 7) | 10 g |

-continued

| Moisturizing milk for the body | | |
|---|---|---|
| | Emulsified excipient oil in water | 90 g |
| Use: | After-bath or after-sun applications | |

EXAMPLE 21

| Lip protecting balm | | |
|---|---|---|
| Composition: | Lamellar phase with lanosterol (according to Example 11) | 10 g |
| | Fatty excipient | 90 g |
| Use: | Application to the lips for protection against weather conditions | |

EXAMPLE 22

| Stimulating antiwrinkle treatment | | |
|---|---|---|
| Composition: | Embryonic extracts suspension (according to Example 8) | 30 g |
| | Gelled excipient | 70 g |
| Use: | Application to the face once a week | |

Preferably, the solvent used for preparing the pulverulent mixture through atomizing is a non-aqueous solvent.

This explains why the examples only exemplify use of non-aqueous solvents in this regard.

What is claimed is:

1. A method for producing a pulverulent material of at least one amphiphilic lipidic constituent which deteriorates at a predetermined temperature, said material being used in particular for forming hydrated lipidic lamellar phase such as liposomes or the like, said method comprising
dissolving said amphiphilic lipidic constituent in a non-aqueous solvent having a boiling point below said predetermined temperature to form a solution of the same, and
atomizing the thus-formed solution in a flow of hot gaseous fluid above the boiling pont of said non-aqueous solvent and below said predetermined temperature to produce said pulverulent material without damage to said amphiphilic lipidic constituent.

2. A method for producing a pulverulent material of at least one amphiphilic lipidic constituent, said material being used in particular for forming hydrated lipidic lamellar phases such as liposomes or the like, said method comprising
dissolving in a non-aqueous solvent, said amphiphilic lipidic constituent, to form a solution of the same, and
atomizing the thus-formed solution in a flow of hot gaseous fluid to produce said pulverulent material, the initial temperature of sid gaseous fluid being higher than the boiling point of the aforesaid non-aqueoius solvent, and
the temperature of said gaseous fluid in the region of formation of the powder being lower than the temperature of transition of said mixture of amphiphilic lipidic constituent.

3. The method of claim 2, wherein the initial temperature of said gaseous fluid ranges between about 60° C. and about 100° C.

4. The method of claim 2, wherein the weight proportion of said amphiphilic lipidic constituent dissolved in the non-aqueous solvent before atomization is greater than 50%.

5. The method of claim 4, characterized in that the weight proportion of amphiphilic lipidic constituent is greater than 70%.

6. The method of claim 2, characterized in that said amphiphilic lipidic constituent possesses biological activity.

7. The method of claim 2, wherein said amphiphilic lipidic constituent is selected from the group consisting of glycolipids, phospholipids, and phosphaminolipids.

8. The method of claim 7, wherein said amphiphilic lipidic constituent is selected from the group consisting of soya or egg lecithin, phosphatidylserin, cerebroside and sphyngomyelin.

9. A method for producing a pulverulent material of at least one amphiphilic lipidic constituent and at least one constituent of at least partially hydrophobic character, said material being used in particular for forming hydrated lipidic lamellar phases such as liposomes or the like,
said method comprising
dissolving in a non-aqueous solvent, said amphiphilic lipidic constituent and said at least partially hydrophobic constituent, to form a solution of the same, and
atomizing the thus-formed solution in a flow of hot gaseous fluid to produce said pulverulent material.

10. The method of claim 9, wherein said at least partially hydrophobic constituent is selected from the group consisting of sterols or esters thereof, alphatic fatty acids or esters thereof, triterpenic fatty acids or esters thereof, primary or secondary fatty alcohols or esters thereof, alphatic fatty amines, aminoacids acylated with a fatty acid, polypeptides, vitamins, extracts of animal or vegetable origin, phenols and phenols which have one or several substituents selected from the group consisting of alkoxy, alkyl comprising 1 to 4 carbon atoms, carboxy or formyl groups.

11. The method of claim 10, wherein said at least partially hydrophobic constituent is selected from the group consisting of cholesterol, β-sitosterol, oestradiol, lanosterol, stigmaterol, γ-oryzanol, stearic acid, xymeninic acid, isopropyl myristate, glycyrrhetinic acid, dicetyl phosphate, stearylamine, stearoly-L-glutamic acid, elastin hydrolysate polypeptides, a tocopherol, embryonic extracts, aloe extracts, or vanilline.

12. The method of claim 2, wherein said non-aqueous solvent is an individual, homogeneous solvent or a miscible mixture of a plurality of solvents, at least one of which is a non-aqueous solvent, the individual, homogeneous, non-aqueous solvent or mixture of solvents having a boiling point lower than the temperature of deterioration of the dissolved amphiphilic constituent.

13. The method of claim 2, wherein the gaseous fluid used to atomize said solution is a gas which is essentially chemically inert in regard to the constituents dissolved in said solution.

14. The method of claim 2, characterized in that said amphiphilic lipidic constituent possesses organoleptic properties.

15. A method for producing a pulverulent material of at least one amphiphilic lipidic constituent, said material being used in particular for forming hydrated lipidic lamellar phases such as liposomes or the like, comprising dissolving in a non-aqueous solvent, said amphiphilic lipidic constituent to form a solution of the same, and atomizing the thus-formed solution in a flow of hot gaseous fluid to produce said pulverent material, said solvent being selected from the group consisting of chloroform, methanol, ethanol, dichloromethane, a material of chloroform with methanol, and a mixture of chloroform with ethanol.

16. A method for producing a pulverent material of at least one amphiphilic lipidic constituent, said material being used in particular for forming hydrated lipidic lamellar phases such as liposomes or the like, comprising dissolving in a non-aqueous solvent, said amphiphilic lipidic constituent to form a solution of said constituent, adding to said solution of said amphiphilic lipidic constituent, solid microalveolate particles, thereby obtaining a powder through atomization.

17. A pulverent material of at least one amphiphilic lipidic constituent which is obtained by dissolving in a non-aqueous solvent, said amphiphilic lipidic constituent to form a solution of said constituent and by atomizing said solution in a flow of hot gaseous fluid produce said pulverent mixture.

18. The material of claim 17 which additionally comprises at least one constituent of at least partially hydrophobic character, and is obtained by additionally dissolving said at least partially hydrophobic constituent in said non-aqueous solvent prior to atomizing.

19. A method for producing hydrated lipidic lamellar phases, such as liposomes, comprising dispersing in a suitable aqueous medium, a pulverent material at least one amphiphilic lipidic constituent obtained by dissolving in a non-aqueous solvent said amphiphilic lipidic constitutent to form a solution of said constituent, and in atomizing said solution in a flow of hot gaseous fluid to produce said pulverent material.

20. The method of claim 19, characterized in that the pulverent material is collected directly in said aqueous medium which is subjected to agitation in order to disperse said pulverent mixture.

21. The method of claim 19, characterized in that the pulverent material is dispersed in a predetermined quantity of said aqueous medium in order to obtain a desired weight concentration of the pulverent material.

22. The method of claim 21 wherein said weight concentration of pulverent material in a suspension of hydrated lipidic lamellar phases is equal at most to about 50%.

23. The method of claim 22, wherein the efficiency of encapsulation, in said hydrated lipidic lamellar phases, of said substance dissolved in said aqueous medium ranges between about 20% and about 50%.

24. The method of claim 19, characterized in that said aqueous medium contains at least one substance which possesses biological activity.

25. The method of claim 19 characterized in that said pulverent material is dispersed in a small amount of aqueous medium in order to obtain slightly hydrated lamellar phases.

26. The method of claim 25, wherein the weight concentration of the pulverulent material in said aqueous medium ranges between about 60 and 75%.

27. The method of claim 25, characterized in that said slightly hydrated lamellar phases are obtained by dispersing said pulverent material in said aqueous medium by crushing.

28. The method of claim 25, characterized in that said slightly hydrated lamellar phase is dispersed in said aqueous medium to obtain a weight concentration of the pulverent material ranging between 0.1 and 10% approximately.

29. The method of claim 28, characterized in that the efficiency of encapsulation in said hydrated lipidic lamellar phases of said substance dissolved in said aqueous medium for the formation of slightly hydrated lamellar phases, is higher than 50% approximately.

30. Hydrated lipidic lamellar phases, obtained by dispersing in a suitable aqueous medium, the pulverent material of at least one amphiphilic lipidic constituent obtained by dissolving in a non-aqueous solvent said amphiphilic lipidic constituent to form a solution of said constituent and by atomizing said solution in a flow of hot gaseous fluid to produce said pulverent material.

31. The phase of claim 30, wherein said pulverent material additionally comprises at least one constituent of at least partially hydrophobic character, which is dissolved in said non-aqueous solvent prior to atomizing.

32. A pharmaceutical composition containing a therapeutically efficient proportion of an active constituent which is incorporated or encapsulated in hydrated lipidic lamellar phases obtained by dispersing a pulverent material of at least one amphiphilic lipidic constituent obtained by dissolving in a non-aqueus solvent, said amphiphilic lipidic constituent to form a solution of said constituent and by atomizing said solution in a flow of hot gaseous fluid to produce said pulverent material; said lamellar phases being mixed with at least one pharmaceutically acceptable excipient or vehicle.

33. A composition for use as a cosmetic product, comprising an efficient quantity of an active substance which is incorporated or encapsulated in hydrated lipidic lamellar phases obtained by dispersing a pulverent material of at least one amphiphilic lipidic constituent obtained by dissolving in a non-aqueous solvent, said amphiphilic lipidic constituent to form a solution of said constituent and by atomizing said solution in a flow of hot gaseous fluid to produce said pulverent material, excipient or vehicle.

34. The method of claim 19, characterized in that said aqueous medium contains at least one substance which possesses organoleptic properties.

* * * * *